(12) United States Patent
Buchholz et al.

(10) Patent No.: US 6,512,145 B1
(45) Date of Patent: *Jan. 28, 2003

(54) METHOD FOR THE CATALYTIC, ASYMMETRIC DISUBSTITUTION OF CARBOXYLIC ACID AMIDES WITH TWO DIFFERENT GRIGNARD REAGENTS

(75) Inventors: Herwig Buchholz, Frankfurt (DE); Urs Welz-Biermann, Mannheim (DE)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/719,823

(22) PCT Filed: Jun. 18, 1999

(86) PCT No.: PCT/EP99/04250

§ 371 (c)(1),
(2), (4) Date: Feb. 23, 2001

(87) PCT Pub. No.: WO99/65858

PCT Pub. Date: Dec. 23, 1999

(30) Foreign Application Priority Data

Jun. 18, 1998 (DE) .......................... 198 27 163

(51) Int. Cl.$^7$ ............................. C07C 211/01
(52) U.S. Cl. .................. 564/374; 564/373; 564/391; 556/12; 556/95
(58) Field of Search ................ 564/373, 374, 564/391; 556/12, 95

(56) References Cited

PUBLICATIONS

"Houben–Weyl, Methoden Der Organischen Chemie, vol. XI/1, S. 820–823" 1957, Georg Thieme Verlag, Stuttgart, DE XP002117680 Seite 820, Absatz 2 –Seite 823, Absatz 1. Beilsteins Handbuch der Organischen Chemie, vierte Auflage, drittes und viertes Ergaenzungswerk, Bd 20, erster Teil, S. 316"1977, Springer–Verlag, Berlin Heidelberg. New York XP002117681 Seite 316, Absatz 3.

Kuffner F. et al.: "Ueber hochverzweigte aliphatische Verbindungend" Monatshefte FueR Chemie, Bd. 93, 1962, Seiten 499–475, XP002117676 in der Anmeldung erwaehnt.

Manfred T. Reetz et al.: "Stereooselective addition of organotitanium reagents to carbonyl compounds" Chemische Berichte., Bd. 118, Nr. 4, 1985, Seiten 1441–1454, XP002117771 Verlag Chemie GMBH Weinheim., DE ISSN: 0009–2940.

Manfred T. Reetz et al.: "Chemoselective addition of organotitanium reagents to carbonyl compounds" Chemische Berichte., Bd. 118, Nr. 4, 1985, Seiten 1421–1440, XP002117770 Verlag Chemie GMBH. Weinheim., DE ISSN: 0009–2940.

Vladimir Chaplinski et al.: "Eine nuetzliche Synthese von Cyclopropylaminen aus Carbonsaeurediakylamiden" Angewandte Chemie., Bd. 108, Nr. 4, 1996, Seiten 491–492, XP002117735 VCH Verlagsgesellschaft, Weinheim., DE ISSN: 0044–8249.

Yuying C. Hwang et al.: "A synthesis of &–substituted amines" Journal of Organic Chemistry., Bd. 50, Nr. 20, 1985, Seiten 3885–3890, XP002117673 Easton US.

Vladimir Chaplinski et al.: "A new versatile reagent for the synthesis of cyclopropylamines . . . " Synlett., 1997, Seiten 111–114, XP002117679 Thieme Verlag, Stuttgart., DE ISSN: 0936–5214.

Jerry March: "Advanced organic chemistry" 1985, John Wiley, New York. Chischester. Brisbane. Toronto. Singapor XP002117736 Seite 825, Absatz 3.

*Primary Examiner*—Ceila Chang
*Assistant Examiner*—Sonya Wright
(74) *Attorney, Agent, or Firm*—Millen, White, Zelano & Branigan, P.C.

(57) ABSTRACT

The invention relates to a method for asymmetrically disubstituting carboxylic acid amides on the geminal carbonyl-C-atom using two grignard reagents in the presence of a metal alcoholate compound used as a catalyst and in the presence of another organometalic compound used as a co-catalyst.

10 Claims, No Drawings

METHOD FOR THE CATALYTIC, ASYMMETRIC DISUBSTITUTION OF CARBOXYLIC ACID AMIDES WITH TWO DIFFERENT GRIGNARD REAGENTS

This application is a 371 of PCT/EP99/04250 filed Jun. 18, 1999.

The present invention relates to a process for disubstituting carboxamides using 2 different Grignard reagents in the presence of an organometallic compound as catalyst and a further organometallic compound as cocatalyst.

It is already known from the prior art, in particular from the publication in Monatsheften Chem. 93, pages 469 to 475 (1962), that asymmetric alkylated amines are obtained in the reaction of carboxamides such as formamide with two different Grignard reagents. The yield of these products is so low (at most 15%) that these reaction products can only be referred to as byproducts.

Accordingly, it was the object of the invention to prepare asymmetrically substituted amino compounds not only as byproducts in the reaction of carboxamides with 2 different Grignard reagents, but in an acceptable yield and sufficient options for varying the substituents.

Using the process according to the invention, it is possible to prepare asymmetrically substituted amino compounds with a considerably improved yield.

Accordingly, the present invention provides a process for preparing compounds of the general formula (I)

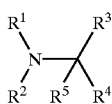  (I)

in which
  $R^1$, $R^2$ and $R^3$ independently of one another are H, A, Ar, —Si($R^6$)$_3$, —Sn($R^6$)$_3$, —S$R^7$, —O$R^7$, —N$R^8R^9$ or $R^1$ and $R^2$ or $R^1$ and $R^3$ or $R^8$ and $R^9$ can be attached to one another and together form a cyclic ring having 3 to 8 C atoms which optionally contains, in addition to nitrogen, at least one further heteroatom selected from the group consisting of —S—, —O— and —N$R^6$—,
  $R^4$ and $R^5$ are A, Ar, —Si($R^6$)$_3$, —Sn($R^6$)$_3$, —S$R^7$, —O$R^7$, —N$R^8R^9$, in which $R^8$ and $R^9$ are as defined above or $R^8$ and $R^9$ are attached to one another and together form a cyclic ring having 3 to 8 C atoms which optionally contains, in addition to one nitrogen atom, at least one heteroatom selected from the group consisting of —S—, —O— and —N$R^6$—;
  or where two radicals $R^4$ are attached to one another and together form a cyclic ring having 3 to 8 C atoms which. optionally contains, in addition to one nitrogen atom, at least one heteroatom selected from the group consisting of —S—, —O— and —N$R^6$,
  with the proviso that $R^4$ and $R^5$ in the β position may have at most one hydrogen atom in each case,
  $R^6$, $R^7$, $R^8$ and $R^9$ independently of one another are A or Ar,
  A is a straight-chain or branched alkyl radical having from 1 to 10 C atoms, a straight-chain or branched alkenyl radical having 2 to 10 C atoms, or a straight-chain or branched alkynyl radical having 2–10 C atoms or a substituted or unsubstituted cycloalkyl radical having 3–8 C atoms, or a mono- or polyunsaturated cycloalkyl radical having 3–8 C atoms, and Ar is a substituted or unsubstituted aryl radical having 6–20 C atoms, characterized in that a compound of the general formula (II)

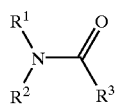  (II)

in which $R^1$, $R^2$ and $R^3$ have the meanings given above for the formula (I) is reacted with a nucleophilic reagent of the general formula (IIIa) and a nucleophilic reagent of the general formula (IIIb)

Z—$R^4$  (IIIa)

Z—$R^5$  (IIIb)

in which
  $R^4$ and $R^5$ have the meaning given for the formula (I), and
  Z is Li or MgX where
  X is Hal and
  Hal is Cl, Br or I.

According to the invention, the process is carried out in the presence of catalytic amounts of a metal alkoxide of the general formula (VI):

$MX_{4-n}(OR)_n$  (IV)

in which
  M is titanium, zirconium or hafnium,
  X is Cl, Br, I and
  R is alkyl having 1 to 10 C atoms or aryl having 6 to 20 C atoms
  n an integer from 1 to 4.

Preference is given to using metal alkoxides in which R is isopropyl. Particular preference is given to using the metal alkoxide Ti(OiPr)$_4$ in which iPr is an isopropyl radical.

The present invention also provides a corresponding process which is carried out in the presence of a cocatalyst. Accordingly, the present invention includes a process which is carried out using metal isopropoxides and alkylsilyl halides as cocatalysts; i.e. metal isopropoxldes of the general formula (V) and alkylsilyl halides of the general formula (VI)

$M'^{(s+)}$(O-isopropyl)$_s$  (V)

$R_3SiX$  (VI)

or of the general formula (VII)

$R_o$—(X)$_m$—Si—Y—(Si)$_p$—(X)$_q$—$R_o$  (VII)

in which
  M' is Al, Ca, Na, K, Si or Mg, preferably Mg or Na,
  s is an integer from 1 to 4 and is the oxidation stage of the metal,
  R is alkyl having 1 to 10 C atoms or aryl having 6 to 20 C atoms,
  X is F, Cl, Br, CN,
  m is 0, 1,
  n is 1 to 10,
  o is 0, 2, 3, p is 0, 1 and q is 0, 1, with the proviso that o=3 and Y≠(CH$_2$)$_n$ if m=0.

Thus, the invention also provides a process, which is characterized in that a) a carboxamide of the general formula (II), 1–15 mol %, based on the carboxamide, of a metal alkoxide selected from the group consisting of titanium alkoxide, zirconium alkoxide and hafnium alkoxide and, if appropriate, a cocatalyst are initially charged at room temperature under an atmosphere of inert gas in a solvent selected from the group consisting of toluene, THF, n-hexane, benzene and diethyl ether, b) a solution comprising a nucleophilic reagent of the general formula (IIIa) or (IIIb) is added dropwise and c) the mixture is allowed to react with stirring and, after the reaction has ended, worked up in a customary manner.

Experiments have shown that, using two nucleophilic reagents of the general formulae (IIIa) and (IIIb), which may be Grignard reagents and are added as such to the reaction mixture, it is possible to convert carboxamides of the general formula (II) in the presence of catalytic amounts of titanium alkoxide, zirconium alkoxide or hafnium alkoxide in a simple manner into asymmetrically substituted compounds of the general formula (I).

According to the invention, using the process described herein, it is possible to convert, with good yields, carboxamides of the general formula (II) in which $R^1$, $R^2$ and $R^3$ independently of one another can have the following meanings:

H or

A i.e. branched or unbranched alkyl having 1–10 C atoms, such as methyl, ethyl, n- or isopropyl, n-, sec- or t-butyl, pentyl, hexyl, heptyl, octyl, nonyl, decyl and suitable isomers thereof, or cycloalkyl having 3–8 C atoms, such as cyclopropyl, cyclobutyl, cyclopentyl, cyclohexyl, cycloheptyl, cyclooctyl, and corresponding methyl- or ethyl-substituted cycloalkyl groups, or mono- or polyunsaturated cycloalkyl groups, such as cyclopentenyl or cyclopentadienyl, or branched or unbranched alkenyl having 2 to 10 C atoms, such as allyl, vinyl, isopropenyl, propenyl, or branched or unbranched alkynyl having 2 to 10 C atoms, such as ethynyl, propynyl, or aryl having 6 to 20 C atoms which is either unsubstituted or mono- or polysubstituted, such as phenyl, naphthyl, anthryl, phenanhryl, mono- or polysubstituted by substituents selected from the group consisting of NO$_2$, F, Cl, Br, NH$_2$, NHA, NA$_2$, OH and DA, where A can have the meanings given above, can be mono-, poly-, or fully halogenated, preferably fluorinated, or aralkenyl or aralkynyl, where the aryl, alkenyl and alkynyl groups can in each case have the given meanings, such as, for example, in phenylethynyl.

Good yields are in particular also obtained using carboxamides in which $R^1$ and $R^2$ or $R^1$ and $R^3$ together form a cyclic ring having 3–8 C atoms which, in addition to nitrogen, contains further heteroatoms, such as —S—, —O— or —NR$^6$—. Particular preference is given here to compounds in which $R^1$ and $R^2$ or $R^1$ and $R^3$ form a simple cyclic ring which includes the nitrogen of the carboxamide or in which $R^1$ and $R^2$ or $R^1$ and $R^3$ form a cyclic ring which contains, as further heteroatom, an oxygen atom.

Thus, hugh yields are obtained in this manner when the starting materials used are compounds such as, for example,

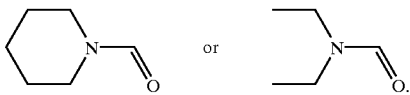

The nucleophilic reagent used can be Grignard reagents or organolithium compounds of the general formulae (IIIa) and (IIIb), in which the radicals $R^4$ and $R^5$ are preferably an alkyl radical having 1 to 10 C atoms, such as methyl, ethyl, n- or isopropyl, n-, sec- or t-butyl, pentyl, hexyl, heptyl, octyl, nonyl, decyl and suitable isomers thereof, or cycloalkyl having 3–8 C atoms, such as cyclopropyl, cyclobutyl, cyclopentyl, cyclohexyl, cycloheptyl, cyclooctyl or corresponding methyl- or ethyl-substituted cycloalkyl groups or mono- or polyunsaturated cycloalkyl groups, such as cyclopentenyl or cyclopentadienyl, or branched or unbranched alkenyl having 2 to 10 C atoms, such as allyl, vinyl, isopropenyl, propenyl, or branched or unbranched alkynyl having 2 to 10 C atoms, such as ethynyl, propynyl, or are an aryl radical having 6 to 20 C atoms which is either unsubstituted or mono- or polysubstituted, such as phenyl, napthyl, anthryl, phenanthryl, mono- or polysubstituted by substituents selected from the group consisting of NO$_2$, F, Cl, Br, NH$_2$, NHA, NA$_2$, OH and OA, where A can have the meanings given above, can be mono-, poly- or fully halogenated, preferably fluorinated, or are an aralkyl radical having 7 to 20 C atoms, such as benzyl, optionally mono- or polysubstituted by substituents selected from the group consisting of NO$_2$, F, Cl, Br, NH$_2$, NHA, NA$_2$, OH and OA, where A can have the meanings given above, can be mono-, poly- or fully halogenated, preferably fluorinated, or are an aralkenyl or aralkynyl radical, where the aryl, alkenyl and alkynyl group can in each case have the given meanings, such as, for example, in phenylethynyl.

Furthermore, the radicals $R^4$ and $R^5$ in the general formulae (IIIa) and (IIIb) can be —Si(R$^6$)$_3$, —Sn(R$^6$)$_3$, —SR$^7$, —OR$^7$, —NR$^8$R$^9$, in which R$^6$, R$^7$, R$^8$ and R$^9$ independently of one another can have the abovementioned meanings or R$^8$ and R$^9$ are attached to one another and together form a cyclic ring having 3 to 8 C atoms which may optionally, in addition to a nitrogen atom, contain at least one heteroatom selected from the group consisting of —S—, —O— and —NR$^6$—.

The radical Z in the general formulae (IIIa) and (IIIb) preferably represents a radical MgX where X is Cl or Br, or the radical Z is lithium.

Particular preference according to the invention is given to using Grignard reagents such as: methylmagnesium bromide, ethylmagnesium bromide, n- or isopropylmagnesium bromide, iso-, sec- or tert-butylmagnesium bromide, n-hexylmagnesium bromide, cyclohexylmagnesium chloride, allylmagnesium bromide, vinylmagnesium bromide, cyclopentylmagnesium bromide, cyclopentylmagnesium chloride, phenylmagnesium bromide, benzylmagnesium chloride, for the reaction.

Furthermore, it was found that only if a cocatalyst is added, the geminal asymmetric dialkylation reactions according to the invention start even at room temperature and result in the complete conversion or the starting materials in a relatively short reaction time.

Suitable cocatalysts for this reaction are metal isopropoxides and alkylsilyl halides. Particularly suitable are metal isopropoxides of the general formula (V) and alkylsilyl halides of the general formula (VI)

$$M'^{(s+)}(\text{O-isopropyl})_s \quad \text{(V)}$$

$$R_3SiX \quad \text{(VI)}$$

or of the general formula (VII)

$$R_o-(X)_m-Si-Y-(Si)_p-(X)_q-R_o \quad \text{(VII)}$$

in which

M' is Al, Ca, Na, K, Si or Mg, preferably Mg or Na, s is an integer from 1 to 4 and is the oxidation stage of the metal, R is alkyl having 1 to 10 C atoms or aryl having 6 to 20 C atoms, X is F, Cl, Br, CN, m is 0, 1, n is 1 to 10, o is 0, 2, 3, p is 0, 1 and q is 0, 1, with the proviso that o=3 and Y≠(CH$_2$)$_n$ if m=0.

Preference is given to using metal isopropoxides in which s is an integer from 1 to 4 and is the oxidation stage of the metal and M' is Al, Ca, Na, K, Si or Mg. Particular preference is given to Mg or Na.

Preference is given to using alkylsilyl halides in which R is alkyl having 1 to 6 C atoms. Particular preference is given to those in which R is alkyl having 1 to 3 C atoms and X is chlorine.

Particularly suitable cocatalysts are, inter alia, the following silicon compounds:

(CH$_3$)$_3$SiCl (CH$_3$)$_2$ClSi(CH$_2$)$_2$SiCl(CH$_3$)$_2$ (CH$_3$)$_2$ClSi(CH$_2$)$_3$CN

[(CH$_3$)$_3$Si]$_2$O

[(CH$_3$)$_3$Si]$_2$NH and

[(CH$_3$)$_3$Si]$_2$.

It has been found that the addition of from 0.7 to 1.2 mol, in particular from 0.9 and 1.1 mol, of a cocatalyst based on one mol of starting material leads to improved results such as, for example, higher yields, lower reaction temperature or shorter reaction times.

As can be demonstrated using examples, under favourable conditions a complete conversion of the carboxamide according to the general equation (Eq. 1) has taken place after just one hour:

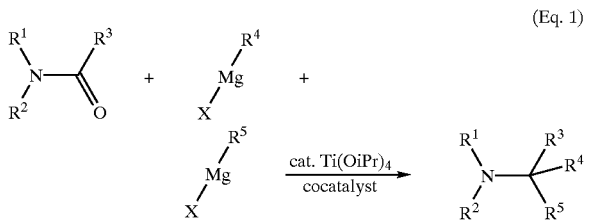

(Eq. 1)

For carrying out the process according to the invention, the catalyst used can be a commercial metal alkoxide selected from the group consisting of titanium alkoxide, zirconium alkoxide and hafnium alkoxide. Preference is given to using titanium tetraisopropoxide. The metal alkoxide, preferably titanium tetraisopropoxide, is used as a solution in a suitable solvent, which is dried beforehand. Suitable solvents are, for example aliphatic or aromatic hydrocarbons or ethers. Preference is given to using solvents selected from the group consisting of toluene, THF, n-hexane, benzene and diethyl ether, which are dried prior to the reaction by methods known to the person skilled in the art. Drying can be carried out with the aid of magnesium sulphate, calcium chloride, sodium, potassium hydroxide or by other methods.

A preferred embodiment of the process according to the invention comprises initially charging the titanium tetraisopropoxide used as catalyst in an amount of from 1 to 15, preferably 1.5 to 14, in particular 2 to 10 and very particularly preferably from 3 to 6 mol %, based on one mol of the amide used as starting material, in the form of a solution adjusted to a temperature of from 10 to 30° C., preferably 15–25° C., particularly preferably to a temperature of about 20° C. Under an atmosphere of inert gas (nitrogen or argon), the starting material, either as such in liquid form or dissolved in a solvent selected from the group consisting of toluene, THF, n-hexane, benzene and diethyl ether, is slowly added dropwise with stirring. An amount of cocatalyst which corresponds to the amount to be reacted is then added dropwise, if required likewise in a solvent. The reaction mixture obtained is stirred for a short period, i.e. for a few minutes, at a constant temperature. Such an amount of the nucleophilic reagent of the general formulae (TITa) and (IIIb), in particular Grignard reagents, is then slowly added to the resulting reaction mixture that substitution of the geminal carbonyl C atom by two different substituents, i.e. an asymmetric substitution of the geminal carbonyl C atom, can take place. The addition of the nucleophilic reagents according to the invention prepared by methods generally known to the person skilled in the art should take place at such a rate that the temperature of the reaction mixture does not exceed 50° C. It is advantageous to carry out the addition of the nucleophilic reagents, i.e. of the Grignard reagents or the lithium compounds, with efficient mixing, preferably vigorous stirring. To shift the reaction equilibrium to the side of the desired asymmetrically substituted product, the nucleophilic reagents used, preferably Grignard reagents, are each added in amounts of from 0.7 to 1.2 mol per mole of starting material that participates in the reaction. Preference is given to adding the Grignard reagents in amounts of from 0.9 to 1.1 mol, based on 1 mol of starting material.

After the addition of the Grianard reagents has ended, the reaction mixture is stirred for some time at a constant temperature, until the reaction is brought to completion.

If no cocatalyst s added to the reaction mixture, the reaction temperature can, after addition of the nucleophilic reagents has ended and the mixture has been mixed thoroughly, be adjusted to about 80° C., preferably to from 60 to 70° C., in particular to 65° C.

Thus, by the synthesis according to the invention it is possible to prepare asymmetrically substituted amino compounds of the general formula (I) with good or satisfactory yields within adequate reaction times. In an advantageous manner, it is possible, by adding one of the catalysts in combination with one of the cocatalyst compounds described of the general formulae (V), (VI) or (VII), to reduce the reaction times considerably, in. the most favourable case to one hour, without this resulting in a reduction in the yields obtained.

Thus, the present invention also provides the use of a catalyst system comprising a metal alkoxide selected from the group consisting of titanium alkoxide, zirconium alkoxide and hafnium alkoxide as catalyst and a compound of the general formulae (V), (VI) or (VII) with the meanings given above, and the use of this catalyst system for preparing the asymmetrically substituted compounds of the general formula (I).

For example, 5 mmol of starting material are, at 20° C. and under an atmosphere of inert gas, added dropwise with stirring to a solution of 3 mol % of titanium tetraisopropoxide in 40 ml of dried tetrahydrofuran. 5 mmol of cocatalyst, likewise taken up in dried tetrahydrofuran, are added slowly with stirring to this mixture. The mixture is stirred at 20° C. for 5 minutes, and a solution of 6 mmol each of two different Grignard reagents is then added at such a rate that the temperature of the reaction mixture does not exceed 50° C. Stirring is continued for one hour, until the reaction has gone to completion.

After the reaction according to the invention, work-up of the reaction mixture can be carried but in a manner known to the person skilled in the art.

Here, the products can be precipitated as salts using solutions of hydrochloric acid, for example a 1 molar ethereal solution of hydrochloric acid, and be filtered off and, if required, purified by recrystallization.

To remove the Lewis acid, it is possible, for example, to add a suitable amount of saturated ammonium chloride solution and water, followed by further vigorous stirring for a plurality of hours (1–3 hours). The resulting precipitate is separated off and washed with a little ether, preferably diethyl ether. The filtrate is made alkaline (pH>10) by addition of a suitable base, such as an NaOH, KOH, sodium carbonate or potassium carbonate solution, preferably sodium hydroxide solution. The phases that are formed are then separated, and the aqueous phase is extracted repeatedly (for example in the special case given above three times with in each case 30 ml) with diethyl ether. The combined organic phases are washed with (for example 15 ml of) saturated sodium chloride solution and can be dried over potassium carbonate, magnesium sulphate or sodium sulphate and filtered.

The products can be purified by various routes using methods known to the person skilled in the art, such as, for example, in the following manner:

1. They are precipitated as hydrochlorides using 1 M ethereal hydrochloric acid solution and filtered off (the resulting product is, if required, purified by recrystallization).

2. The organic phase is extracted repeatedly with a 0.5 M acid solution, preferably an aqueous hydrochloric acid solution. The extract obtained is adjusted to pH>10 using bases, preferably 2 M aqueous sodium hydroxide solution, and extracted at least once, preferably repeatedly, with diethyl ether. The resulting organic phases, which contain the reaction product, can be dried, if appropriate, over potassium carbonate, magnesium sulphate or sodium sulphate and be freed from the organic solvent under reduced pressure.

3. Furthermore, it is possible to isolate the reaction product by removing the organic solvent under reduced pressure and separating the residue that remains by column chromatography, to isolate the reaction product.

In the general description of the process procedure given above, the Grignard reagents can also be replaced by the corresponding lithium compounds. The corresponding lithium compounds, like the Grignard reagents, can be prepared by methods generally known to the person skilled in the art, and they can be reacted according to the invention in the same manner as described above.

The compounds of the general formula (I) prepared according to the invention can be used, for example, as intermediates in the preparation of sulphur- or selenium-containing amines for the chiral catalysis of diethyl zinc syntheses (literature: Werth, Thomas; Tetrahydron Lett. 36; 1995, 7849–7852, Werth, Thomas et al. Helv. Chim. Acta 79, 1996, 1957–1966).

To illustrate and better understand the present invention, examples are given below. However, owing to the general validity of the described principle of the invention, they are not meant to reduce the scope of the present application to just these examples.

EXAMPLES

Titanium-tetraisopropoxide-induced asymmetric dialkylation of carboxamides using 2 different Grignard reagents According to the reaction shown in Equation 1, the following reactions were carried out using one equivalent of $(CH_3)_3SiCl$ as cocatalyst:

TABLE 1

$Ti(OiPr)_4$-induced reaction of carboxamides with $R^4MgX$ and $R^5MgX$.

(Eq. 1)

$$\begin{array}{c} R^1 \\ \diagdown \\ N-C \\ \diagup \diagdown \\ R^2 \quad O \end{array} \begin{array}{c} R^3 \\ \end{array} + \begin{array}{c} R^4 \\ \diagup \\ Mg \\ \diagdown \\ X \end{array} + \begin{array}{c} R^5 \\ \diagup \\ Mg \\ \diagdown \\ X \end{array} \xrightarrow[\text{cocatalyst}]{\text{cat. Ti(OiPr)}_4} \begin{array}{c} R^1 \quad R^3 \\ \diagdown \quad \diagup \\ N-C-R^4 \\ \diagup \quad \diagdown \\ R^2 \quad R^5 \end{array}$$

| Amide | Product | Yield | $R^4MgX$/ $R^5MgX$ | Reactions conditions |
|---|---|---|---|---|
|  |  | 71% | MeMgBr/ PhMgBr | 1 h/25° C./ 3 mol % $Ti(OiPr)_4$/5 mmol cocat |

TABLE 1-continued

Ti(OiPr)$_4$-induced reaction of carboxamides with R$^4$MgX and R$^5$MgX.

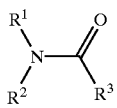
(Eq. 1)

| Amide | Product | Yield | R$^4$MgX/ R$^5$MgX | Reactions conditions |
|---|---|---|---|---|
| 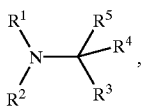 | | 81% | PhMgBr/ BnMgCl | 1 h/RT/ 3 mol % Ti(OiPr)$_4$ |
| | | 79% | MeMgBr/ PhMgBr | 3 mol % Ti(OiPr)$_4$/5 mmol cocat |

Me = Methyl,
Ph = Phenyl,
iPr = iso-Propyl,
Bn = Benzyl,
cocat = (CH$_3$)$_3$SiCl

What is claimed is:

1. Process for preparing an asymmetric compound of the formula

 (I)

in which

R$^1$, R$^2$ and R$^3$ independently of one another are H, A, Ar, —Si(R$^6$)$_3$, —Sn(R$^6$)$_3$, —SR$^7$, —OR$^7$, —NR$^8$R$^9$, R$^4$ and R$^5$ are A, Ar, —Si(R$^6$)$_3$, —Sn(R$^6$)$_3$, —SR$^7$, —OR$^7$, —NR$^8$R$^9$, in which R$^8$, R$^9$ and R$^{10}$ are as defined above, with the proviso that when R$^4$ is A, R$^4$ may not have more than one hydrogen in the β position, and when R$^5$ is A, R$^5$ may not have more than one hydrogen in the β position.

R$^6$, R$^7$, R$^8$ and R$^9$ independently of one another are A or Ar,

A is a straight-chain or branched alkyl radical having from 1 to 10 C atoms, a straight-chain or branched alkenyl radical having 2 to 10 C atoms, or a straight-chain or branched alkynyl radical having 2–10 C atoms or a substituted or unsubstituted cycloalkyl radical having 3–8 C atoms, or a mono- or polyunsaturated cycloalkyl radical having 3–8 C atoms, and Ar is a substituted or unsubstituted aryl radical having 6–20 C atoms, wherein a compound of the general formula (II)

 (II)

in which R$^1$, R$^2$ and R$^3$ have the meanings given above for the formula (I) is reacted with a nucleophilic reagent of the general formula (IIIa) and a nucleophilic reagent of the general formula (IIIb)

Z—R$^4$ (IIIa)

Z—R$^5$ (IIIb)

in which
Z is Li or MgX where
X is Hal and
Hal is Cl, Br or 1,
wherein the process is carried out in the presence of catalytic amounts of a metal alkoxide selected from the group consisting of titanium alkoxide, zirconium alkoxide and hafnium alkoxide,
and wherein the process is carried out in the presence of a cocatalyst.

2. A process according to claim 1, carried out in the presence of a metal isopropoxide or an alkylsilyl halide cocatalyst.

3. Process according to claim 1, wherein the cocatalyst used is a metal isopropoxide of formula (V) or an alkylsilyl halide formula (VI)

M$^{(s+)}$(O-isopropyl)$_s$ (V)

R$_3$SiX (VI)

in which

M' is Al, Ca, Na. K, Si or Mg, s is an integer from 1 to 4 and is the oxidation stage of the metal, R is alkyl having 1 to 10 C atoms or aryl having 6 to 20 C atoms, X is F, Cl, Br, CN, or an alkylsilyl halide of the formula $(CH_3)_2ClSi(CH_2)_2SiCl(CH_3)_2$, $(CH_3)_2ClSi(CH_2)_3CN$, $[(CH_3)_3Si]_2O$, $[(CH_3)_3Si]_2NH$ or $[(CH_3)_3Si]_2$.

4. A process according to claim 1, wherein the catalyst used is a metal alkoxide of the formula (VI)

$$MX_{4-n}(OR)_n \qquad (IV)$$

in which

M is titanium, zirconium or hafnium,

X is Cl, Br, I and

R is alkyl having 1 to 10 C atoms or aryl having 6 to 20 C atoms, n is an integer from 1 to 4.

5. A process according to claim 1, further comprising;

a) initially charging a carboxamide of the general formula (II), 1–15 mol %, based on the carboxamide of the metal alkoxide selected from the group consisting of titanium alkoxide, zirconium alkoxide and hafnium alkoxide and optionally the cocatalyst at 10–30° C. under an atmosphere of inert gas in a solvent selected from the group consisting of toluene, THF, n-hexane, benzene and diethyl ether, b) adding dropwise a solution comprising two different nucleophilic reagents of the general formulae (IIIa) or (IIIb)

in which $R^4$, $R^5$ and X have the meanings given in claim 1 and c) reacting the mixture with stirring.

6. A process according to claim 5, wherein process step a) is carried out at room temperature of from 15 to 25° C.

7. A process according to claim 5, wherein process step a) is carried out at room temperature.

8. A process according to claim 1, wherein the nucleophilic reagent used is a lithium compound of the general formula (IIIa) and (IIIb) in which $R^4$ has the meanings given in claim 1.

9. Process according to claim 1, in that the nucleophilic reagents used are compounds of the general formulae (IIIa) and (IIIb) in which $R^4$ and $R^5$ are methyl, ethyl, n- or isopropyl, iso-, sec- or tert-butyl, n-hexyl, cyclopentyl, cyclohexyl, allyl, vinyl, phenyl or benzyl.

10. Process according to claim 1, in that the compound that is reacted is a compound of the general formula (II) in which $R^1$, $R^2$ and $R^3$ independently of one another are H, methyl, ethyl, n- or isopropyl, iso-, sec- or tert-butyl, n-hexyl, phenyl or benzyl.

* * * * *

UNITED STATES PATENT AND TRADEMARK OFFICE
CERTIFICATE OF CORRECTION

PATENT NO. : 6,512,145 B1
DATED : January 28, 2003
INVENTOR(S) : Herwig Buchholz et al.

It is certified that error appears in the above-identified patent and that said Letters Patent is hereby corrected as shown below:

Column 9,
Line 53, reads "position." should read -- position, --.

Column 10,
Line 64, reads "halide formula" should read -- halide of formula --.

Column 11,
Line 17, reads "(VI)" should read -- (IV) --.

Signed and Sealed this

Eighteenth Day of October, 2005

JON W. DUDAS
*Director of the United States Patent and Trademark Office*